(12) United States Patent
Shu (10) Patent No.: US 8,067,636 B2
(45) Date of Patent: Nov. 29, 2011

(54) DIHYDRAZIDE COMPOUNDS, PREPARATION AND USES THEREOF

(75) Inventor: Xiaozheng Shu, Shanghai (CN)

(73) Assignee: Bioregen Biomedical (Shanghai) Co., Ltd, Shanghai (CN)

( * ) Notice: Subject to any disclaimer, the term of this patent is extended or adjusted under 35 U.S.C. 154(b) by 266 days.

(21) Appl. No.: 12/516,108

(22) PCT Filed: Sep. 17, 2007

(86) PCT No.: PCT/CN2007/002740
§ 371 (c)(1),
(2), (4) Date: May 22, 2009

(87) PCT Pub. No.: WO2008/061427
PCT Pub. Date: May 29, 2008

(65) Prior Publication Data
US 2010/0048952 A1    Feb. 25, 2010

(30) Foreign Application Priority Data
Nov. 24, 2006 (CN) .......................... 2006 1 0118715

(51) Int. Cl.
*C07C 243/14* (2006.01)
*C07C 233/05* (2006.01)
*A61K 31/16* (2006.01)

(52) U.S. Cl. ......... 564/151; 564/149; 514/614; 514/615

(58) Field of Classification Search .................. 564/149, 564/151; 514/614, 615
See application file for complete search history.

(56) References Cited

U.S. PATENT DOCUMENTS 4,882,399 A    11/1989   Tesoro et al.
6,924,312 B2 *  8/2005   Koya et al. .................... 514/614

* cited by examiner

*Primary Examiner* — Shailendra Kumar
(74) *Attorney, Agent, or Firm* — Birch, Stewart, Kolasch & Birch, LLP (57) ABSTRACT

Disclosed are dihydrazide compounds having formula (I) or (II), wherein $R_1$-$R_4$ are alkylene, substituted alkylene, aryl or polyether radical. The preparation and uses for producing medical hydrogel and medicine controlled releasing carrier of said dihydrazide compounds are provided.

10 Claims, 2 Drawing Sheets

Fig.1 a: 2.86 ppm b: 2.52 ppm c: 8.19 ppm d: 3.63 ppm e: 9.01 ppm f: 4.17 ppm

Fig. 2

DIHYDRAZIDE COMPOUNDS, PREPARATION AND USES THEREOF

This application is a 371 of PCT/CN2007/002740, filed Sep. 17, 2007.

TECHNICAL FIELD

The invention relates to compounds, especially to novel dihydrazide compounds. The invention also involves the synthesis method and uses thereof.

BACKGROUND ART

Dihydrazides, those compounds containing two hydrazide functional groups, are widely used as chemical modifiers and cross-linking agents and play important roles in biomedicine, new material science and other fields. Dihydrazide containing disulfide bond, a new type of hydrazide developed in recent years, endows the cross-linked products with special properties by introducing disulfide bonds while being used for chemical modification and chemical crosslinking of materials. For example, Tesoro et al. in the U.S. Pat. No. 4,882,399 used dithiodipropionic acid dihydrazide to prepare epoxy resins having reversible crosslinks. Shu et al. in *Biomacromolecules*, 3, 1304, 2002 reported the synthesis of dithiodipropionic acid dihydrazide and dithiodibutanoic acid dihydrazide. So far, however, as for this type of dihydrazide, only above mentioned several aliphatic and aromatic dihydrazides containing disulfide bond is reported, which cannot meet the demand in new chemical modification and chemical cross-linking of materials.

CONTENTS OF THE INVENTION

The principle object of the invention is to provide a new class of dihydrazide compounds containing disulfide bond.

Another object is to provide the preparation methods for above mentioned dihydrazide compounds.

Another object is to provide the application of above mentioned dihydrazide compounds in the preparation of medical hydrogel and drug delivery carrier.

The new dihydrazide compounds containing disulfide bond by this invention can be represented as the following general formula (I) or (II):

Wherein, $R_1$, $R_2$, $R_3$ and $R_4$ are selected independently from an alkylene group, a substituted alkylene group, an arylene group, a polyether backbone etc.; $R_1$, $R_2$, $R_3$ and $R_4$ may have the completely same chemical structures, or totally different chemical structures, or some of them have the same chemical structures and the others have the different chemical structures.

The above mentioned alkylene group refers to —$(CH_2)_n$— (n is an integer of 1~15), that is, to the straight-chain alkylene group having 1~15 carbon atoms, and preferably to those having 1~8 carbon atoms.

The above mentioned substituted alkylene group refers to the above mentioned alkylene group that at least one of their hydrogen atoms was substituted by lower alkyl, hydroxyl group, amino, alkoxyl, phenyl, ester group etc.

The above mentioned arylene groups refer to phenylene group, naphthylene group etc., and preferably to phenylene group.

The above mentioned polyether backbone refers to —[(CHR)nO]m-, wherein R is a lower alkyl, n is an integer of 1-4, m is an integer of 1-500. The preferred R is a hydrogen atom, while n equals to 2, 3 or 4.

The above mentioned lower alkyl refers to those straight-chain or branched-chain alkyl groups having 1-8 carbon atoms e.g. methyl, ethyl, propyl, isopropyl, butyl, isobutyl, tert-butyl, sec-butyl, amyl, neopentyl, hexyl, heptyl, octyl etc. The straight-chain or branched-chain alkyls having 1-4 carbon atoms, especially methyl, ethyl and propyl are preferred.

The above mentioned alkoxyl refers to straight-chain or branched-chain alkoxyl groups having 1-6 carbon atoms e.g. methoxyl, ethoxyl, propoxyl, iso-propoxyl, butoxyl, isobutoxyl, tert-butoxyl, sec-butoxyl, pentoxyl, neopentoxyl, hexoxyl and so on. The straight-chain or branched-chain alkoxyl groups having 1-4 carbon atoms, especially methoxyl and ethoxyl are preferred.

The above mentioned ester group refers to —C(O)OR, wherein R is the above mentioned lower alkyl, and preferably to methoxycarbonyl, ethoxycarbonyl, propoxycarbonyl and butoxycarbonyl.

The preferred compounds in this invention are those that R1, R2, R3 and R4 are alkylene group or phenylene group independently. More preferred compounds are those that R1, R2, R3 and R4 are all C1-C8 alkylene group independently or R1 and R2 are the same phenylene group. The most preferred compounds are those of general formula (I), wherein R1, R2 are the same C2-C4 alkylene group and R3, R4 are the same C1-C8 alkylene group, or those of general formula (II), wherein R1, R2 are the same C1-C8 alkylene group and R3, R4 are the same C1-C8 alkylene group.

The novel dihydrazide compounds containing disulfide bond in this invention can be synthesized from the corresponding diamines having a disulfide linkage or dicarboxylic acids having a disulfide linkage. Wherein, the compound with general formula (I) is synthesized from the corresponding diamine having a disulfide linkage, and the compound with general formula (II) is synthesized from dicarboxylic acid having a disulfide linkage. The following are chemical structures of some diamines having a disulfide linkage or dicarboxylic acids having a disulfide linkage:

anhydride to synthesize disulfide-linked dicarboxylic acid having two amide groups, (2) esterification of above disulfide-linked dicarboxylic acid, and (3) hydrazinolysis of above esterification product of disulfide-linked dicarboxylic acid.

The following is the chemical equation of a synthesis method for preparing the compound with general formula (I) from cystamine which is one of diamine having a disulfide linkage. Cystamine first reacts with dicarboxylic anhydride to generate disulfide-linked dicarboxylic acid having two amide groups, followed by esterification, and finally the hydrazinolysis of the above esterification product generates the compound with general formula (I) (disulfide-linked dihydrazide having two amide groups), wherein R is one of an alkylene group, a substituted alkylene group, an arylene group, a polyether backbone, etc.:

-continued

Wherein, diamines having a disulfide linkage include (1) cystamine, (2) cystine dimethyl ester, (3) cystine diethyl ester, (4) dithiodianiline; and dicarboxylic acids having a disulfide linkage include (5) dithiodiacetic acid, (6) dithiodipropionic acid, (7) dithiodibutanoic acid, (8) dithiodibenzoic acid.

The method for synthesizing the compound with general formula (I) from diamine having a disulfide linkage usually includes the following 3 steps: (1) amine-anhydride reaction between diamine having a disulfide linkage and dicarboxylic The following is the chemical equation of another synthesis method for preparing the compound with general formula (I) from cystamine which is one of diamine having a disulfide linkage, and this method is similar to the above synthesis method. Cystamine first reacts with dicarboxylic anhydride to generate disulfide-linked dicarboxylic acid having two amide groups, which is then activated with carbonyldiimidazole to generate activated ester, and the above ester is performed by hydrazinolysis directly or after ethyl esterification, and thus the compound with general formula (I) (disulfide-linked dihydrazide having two amide groups) is obtained, wherein R is one of an alkylene group, a substituted alkylene group, an arylene group, a polyether backbone, etc.:

The chemical structures of some compounds with general formula (I) that can be synthesized from cystamine as the one of diamine having a disulfide linkage are as follows:

Wherein, compound (1) is dithiodiethanediyldiaminodicarbonyl diacetic acid dihydrazide (abbr. DPCDH); compound (2) is dithiodiethanediyldiaminodicarbonyl dipropi- onic acid (abbr. DSCDH); compound (3) is dithiodiethanediyldiaminodicarbonyl dimethylpropionic acid dihydrazide (abbr. DMPCDH); compound (4) is dithiodiethanediyldiaminodicarbonyl dibutanoic acid dihydrazide (abbr. DGCDH); and compound (5) is dithiodiethanediyldiaminodicarbonyl dipentanoic acid (abbr. DACDH).

The method for preparing the compound with general formula (II) from dicarboxylic acid having a disulfide linkage usually includes the following steps: (1) activation of dicarboxylic acids having a disulfide linkage by carbonyldiimidazole, (2) diamidation reaction between the activated compound of dicarboxylic acid having a disulfide linkage and amino carboxylic acid ester, and (3) hydrazinolysis.

The following is the chemical equation of a synthesis method for the compound with general formula (II) from dithiodipropionic acid as the one of dicarboxylic acid having a disulfide linkage dithiodipropionic acid first reacts with carbonyldiimidazole to generate an activated ester, then reacts with amino carboxylic acid ester to generate disulfide-linked diester having two amide groups, and finally the hydrazinolysis generates disulfide-linked dihydrazide having two amide groups, wherein R is one of an alkylene group, a substituted alkylene group, an arylene group, a polyether backbone, etc.:

The chemical structures of some compounds with general formula (II) which are synthesized from dithiodipropionic acid as the one of dicarboxylic acid having a disulfide linkage are as follows:

(5)

Wherein, compound (1) is dithiodiethanediyldicarbonyldiamino diacetic acid dihydrazide (abbr. DGDTPDH); compound (2) is dithiodiethanediyldicarbonyldiamino dimethylacetic acid dihydrazide (abbr. DADTPDH); compound (3) is dithiodiethanediyldicarbonyldiamino dihydroxylacetic acid dihydrazide (abbr. DHADTPDH); compound (4) is dithiodiethanediyldicarbonyldiamino dipropionic acid dihydrazide (abbr. DPDTPDH); and compound (5) is dithiodiethanediyldicarbonyldiamino dibutanoic acid dihydrazide (abbr. DBDTPDH).

BRIEF DESCRIPTION OF THE DRAWINGS

The FIG. 1 is the hydrogen nuclear magnetic resonance (abbr. 1H-NMR) spectrum and the chemical shift peak assignment of dithiodiethanediyldiaminodicarbonyl dipropionic acid dihydrazide (abbr. DSCDH) in Example 1.

The FIG. 2 is the hydrogen nuclear magnetic resonance (abbr. 1H-NMR) spectrum and the chemical shift peak assignment of dithiodiethanediyldicarbonyldiamino diacetic acid dihydrazide (abbr. DGDTPDH) in Example 4.

THE BEST MODE OF CARRYING OUT THE INVENTION

The following examples may allow the technician in this field to understand the invention more comprehensively, but not form restriction on the invention in any way.

Example 1

Synthesis of Dithiodiethanediyldiaminodicarbonyl Dipropionic Acid Dihydrazide (Abbr. DSCDH)

(1) Synthesis of Dithiodiethanediyldiaminodicarbonyl Dipropionic Acid (abbr. DSC):

Cystamine dihydrochloride 10 g (Aldrich, USA) was dissolved into 150 ml distilled water to give a clear and transparent solution. NaOH (4 mol/L) was added into the above solution until pH 10. Then under magnetic stirring, succinic anhydride 13.3 g (Aldrich, USA) was added, and simultaneously NaOH (4 mol/L) was added to keep solution pH at 7~10. After 2 h reaction at room temperature, HCl (6 mol/L) was added into the solution, the white precipitated product was collected by filtration, washed twice with 200 ml distilled water, and then dried under reduced pressure to give white solid product DSC of approximately 15 g (yield is higher than 90%).

(2) Synthesis of Dithiodiethanediyldiaminodicarbonyl Dipropionic Acid Diethyl Ester (Abbr. DSCDE):

In a 250 ml three-neck round-bottom flask, DSC 10 g, anhydrous alcohol 120 ml and concentrated sulfuric acid 10 drops were added. After refluxed for 2 hours under nitrogen protection, the solution was concentrated under reduced pressure to a volume less than 20 ml. Then the remained solution was transferred into a 250 ml tap funnel, and ethyl acetate 60 ml was added. Then the organic phase was washed with 50 ml water for three times, the aqueous phase was abandoned, and the organic phase was distilled under reduced pressure to give white lardaceous solid product DSCDE of approximately 9.3 g (yield is higher than 80%).

(3) Synthesis of Dithiodiethanediyldiaminodicarbonyl Dipropionic Acid Dihydrazide (Abbr. DSCDH):

In a 150 ml beaker, DSCDE 10 g and alcohol 80 ml were added and dissolved under stirring, and then hydrazine hydrate 10 ml (Aldrich, USA) was added. After overnight reaction, the white precipitated product was collected by filtration, and rinsed for 4 times with 40 ml alcohol. The organic solvent was evaporated at room temperature in a fume hood, and then the product was dried under reduced pressure to give white solid DSCDH of approximately 8 g (yield is higher than 75%).

Characterization of Dithiodiethanediyldiaminodicarbonyl Dipropionic Acid Dihydrazide (Abbr. DSCDH):

Elemental analysis: $C_{12}H_{24}N_6O_4S_2$

| % | Calculated value | Measured value |
|---|---|---|
| C | 37.88 | 37.34 |
| H | 6.36 | 6.27 |
| N | 22.09 | 22.05 |

High resolution mass spectra: calculated value 380.1300, measured value 380.1295.

Figure 1:
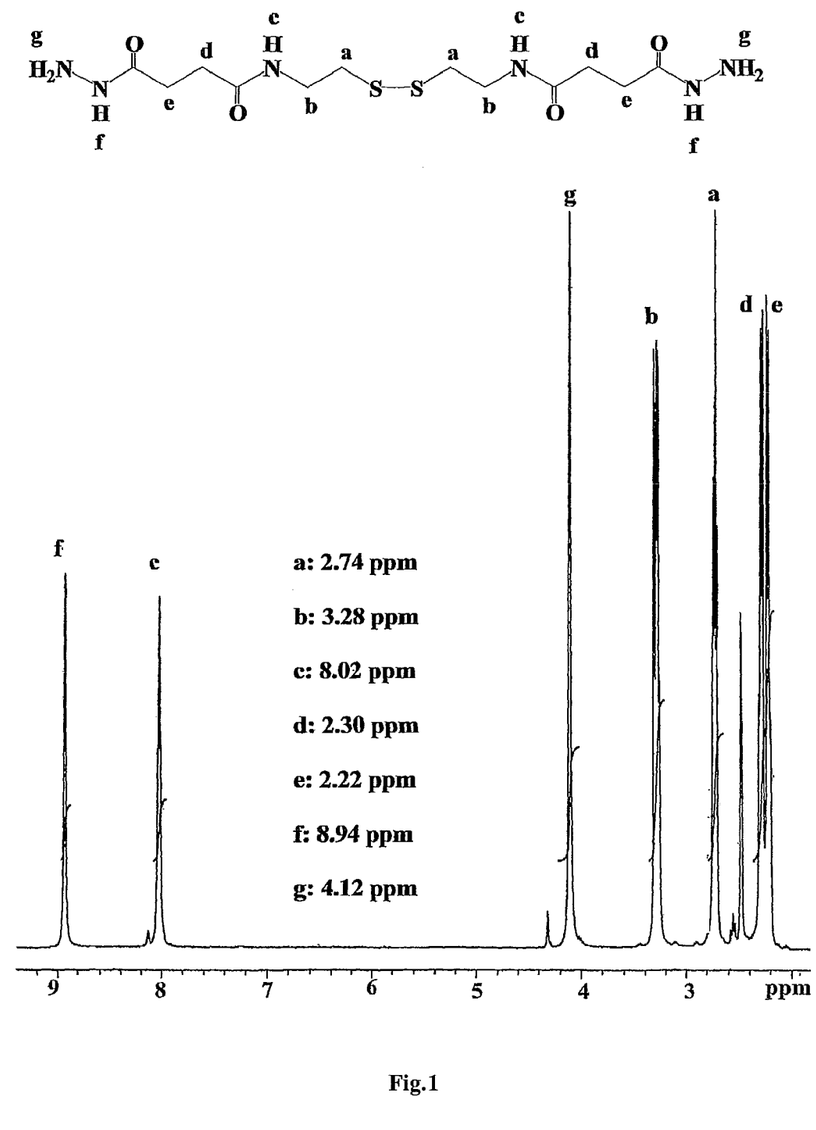

1H-NMR (DMSO-d6): see FIG. 1

Example 2

Synthesis of Dithiodiethanediyldiaminodicarbonyl Dipropionic Acid Dihydrazide (Abbr. DSCDH)

(1) Synthesis of Di-Succinate Dioyl Cystamine (Abbr. DSC): Refer to Example 1.

(2) Synthesis Dithiodiethanediyldiaminodicarbonyl Dipropionic Acid Dicarbonyldiimidazole-Activated Diester (Abbr. DSCDI):

In a 500 ml three-neck round-bottom flask, DSC 10 g, anhydrous DMF 60 ml was added and dissolved under stirring at room temperature, then carbonyldiimidazole 11.2 g (Aldrich, USA) was added, and a lot of CO2 bubbles and white precipitate were generated in the solution. The reaction was performed for 3 hours under reduced pressure at room temperature. Then anhydrous ethyl acetate 200 ml was added to dilute the solution, and the precipitated product was collected by filtration. The precipitate was rinsed twice with 200 ml anhydrous ethyl acetate, and dried under reduced pressure to give white solid product DSCDI of approximately 12 g (yield is higher than 90%).

(3) Synthesis of Dithiodiethanediyldiaminodicarbonyl Dipropionic Acid Dihydrazide (Abbr. DSCDH):

In a 150 ml three-neck round-bottom flask, DSCDI 10 g and alcohol 100 ml was added, and refluxed for 3 hours under nitrogen protection. After the solution was cooled to room temperature, hydrazine hydrate 10 ml was added, and the solution was magnetic stirred overnight. Then the white precipitated product was collected by filtration, and rinsed for 4 times with 40 ml alcohol. The organic solvent was evaporated at room temperature in a fume hood, and then the products was dryed under reduced pressure to give white solid DSCDH of approximately 7 g (yield is higher than 75%).

Example 3

Synthesis of Dithiodiethanediyldiaminodicarbonyl Dibutanoic Acid Dihydrazide (Abbr. DGCDH)

(1) Synthesis of Dithiodiethanediyldiaminodicarbonyl Dibutanoic Acid (abbr. DGC):

Cystamine dihydrochloride 10 g (Aldrich, USA) was dissolved into 150 ml distilled water to give a clear and transparent solution. NaOH (4 mol/L) was added into the above solution until pH 10. Then under magnetic stirring, glutaric anhydride 15.2 g (Aldrich, USA) was added, and simultaneously NaOH (4 mol/L) was added to keep solution pH at 7~10. After 2 h reaction at room temperature, HCl (6 mol/L) was added into the solution, the white precipitated product was collected by filtration, washed twice with 200 ml distilled water, and then dried under reduced pressure to give white solid product DGC of approximately 15.5 g (yield is higher than 90%).

(2) Synthesis of Dithiodiethanediyldiaminodicarbonyl Dibutanoic Acid Diethyl Ester (Abbr. DGCDE):

In a 250 ml three-neck round-bottom flask, DGC 10 g, anhydrous alcohol 120 ml and concentrated sulfuric acid 10 drops was added. After refluxed for 2 hours under nitrogen protection, the solution was concentrated under reduced pressure to a volume less than 20 ml. Then the remained solution was transferred into a 250 ml tap funnel, and ethyl acetate 60 ml was added. Then the organic phase was washed with 50 ml water for three times, the aqueous phase was abandoned, and the organic phase was distilled under reduced pressure to give white lardaceous solid product DGCDE of approximately 9.4 g (yield is higher than 80%).

(3) Synthesis of Dithiodiethanediyldiaminodicarbonyl Dibutanoic Acid Dihydrazide (Abbr. DSCDH):

In a 150 ml beaker, DGCDE 10 g and alcohol 80 ml was added and dissolved under stirring, then hydrazine hydrate 10 ml (Aldrich, USA) was added and reacted overnight. Then the white precipitated product was collected by filtration, and wash for 4 times with 40 ml alcohol. The organic solvent was evaporated at room temperature in a fume hood, and then the products was dried under reduced pressure to give white solid DGCDH of approximately 7.1 g (yield is higher than 75%).

Characterization of Dithiodiethanediyldiaminodicarbonyl Dibutanoic Acid Dihydrazide (Abbr. DGCDH):

Elemental analysis: $C14H_{25}N_6O_4S_2$

| % | Calculated value | Measured value |
|---|---|---|
| C | 41.16 | 40.79 |
| H | 6.91 | 6.82 |
| N | 20.57 | 20.44 |

High resolution mass spectra: calculated value 408.1613, measured value 408.1604.

1H-NMR (DMSO-d6):

| hydrogen | a | b | c | d | e | f | g | h |
|---|---|---|---|---|---|---|---|---|
| δ(ppm) | 2.73 | 3.28 | 8.00 | 2.02 | 1.67 | 1.99 | 8.91 | 4.12 |

Example 4

Synthesis of Dithiodiethanediyldicarbonyldiamino Diacetic Acid Dihydrazide (Abbr. DGDTPDH)

In a 1000 ml beaker, dithiodipropionic acid 10 g (Aldrich, USA) and anhydrous dimethyl formamide 50 ml was added and dissolved under stirring at room temperature, then carbonyldiimidazole 17.0 g (Aldrich, USA) was added into above solution, and a lot of $CO_2$ bubbles and white precipitate were formed in the solution, the reaction was conducted for 3 h under reduced pressure at room temperature. Then glycine ethyl ester hydrochloride 14.7 g (Aldrich, America) was added into above solution, stirring for 1 hour. After that ethyl ether 500 ml was added, kept still for 1 hour, then the organic phase at upper layer was poured with caution and abandoned. After that alcohol 100 ml and hydrazine hydrate 10 ml were added, stirring overnight at room temperature. The white precipitated product was collected by filtration, rinsed twice with 200 ml anhydrous alcohol, and dried under reduced pressure to give slightly yellow solid product DGDTPDH of approximately 8.5 g (yield is about 50%).

Characterization of Dithiodiethanediyldicarbonyldiamino Diacetic Acid Dihydrazide (Abbr. DGDTPDH):

Elemental analysis: $C_{10}H_{20}N_6O_4S_2$

| % | Calculated value | Measured value |
|---|---|---|
| C | 34.08 | 34.99 |
| H | 5.72 | 5.64 |
| N | 23.85 | 23.45 |

High resolution mass spectra: calculated value 352.0987, measured value 352.0981.

Figure 2:
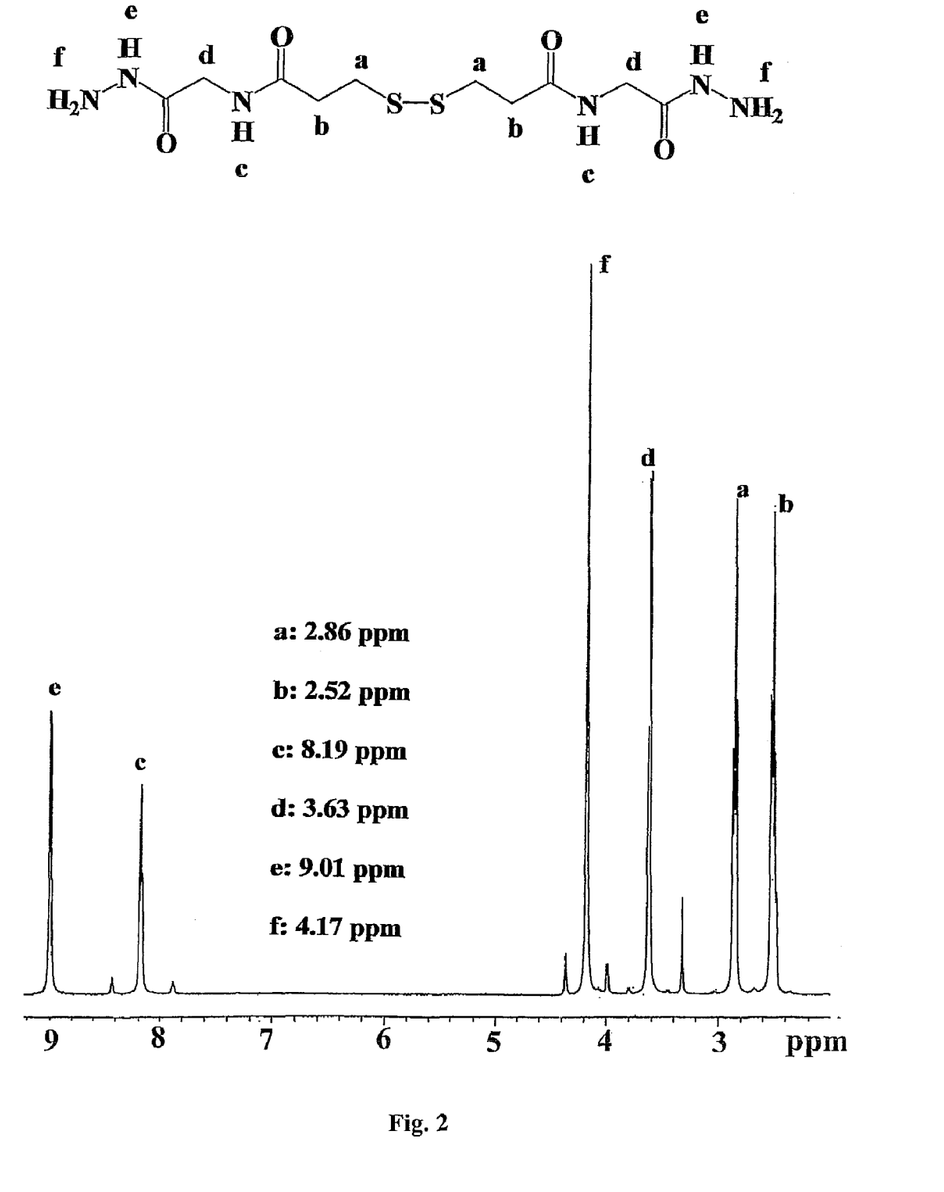

1H-NMR (DMSO-d6): see FIG. 2.

Example 5

Synthesis of Dithiodiethanediyldicarbonyldiamino Dimethylacetic Acid Dihydrazide (Abbr. DADTPDH)

In a 1000 ml beaker, dithiodipropionic acid 10 g (Aldrich, USA) and anhydrous dimethyl formamide 50 ml was added and dissolved under stirring at room temperature, the carbonyldiimidazole 17.0 g (Aldrich, USA) was added into above solution, and a lot of $CO_2$ bubbles and white precipitate were generated in the solution, the reaction was conducted for 3 h under reduced pressure at room temperature. Then aminopropionic acid ethyl ester hydrochloride 14.7 g (Aldrich, America) was added into above solution, stirred for 1 hour. After that ethyl ether 500 ml was added, kept still for 1 hour, the organic phase at upper layer was poured with caution and abandoned. After that alcohol 100 ml and hydrazine hydrate 10 ml were added, stirred overnight at room temperature. The white precipitate product was collected by filtration, rinsed twice with 200 ml anhydrous alcohol, and dried under reduced pressure to give slightly yellow solid product DGDTPDH approximately 7.3 g (yield is about 40%).

Characterization of Dithiodiethanediyldicarbonyldiamino Dimethylacetic Acid Dihydrazide (Abbr. DADTPDH):

Elemental analysis: $C_{12}H_{24}N_6O_4S_2$

| % | Calculated value | Measured value |
|---|---|---|
| C | 37.88 | 37.55 |
| H | 6.36 | 5.89 |
| N | 22.09 | 21.81 |

High resolution mass spectra: calculated value 380.130, measured value 380.1289.

1H-NMR (DMSO-d6):

| hydrogen | a | b | c | d | e | f | g |
|---|---|---|---|---|---|---|---|
| δ(ppm) | 2.84 | 2.42 | 8.02 | 3.20 | 2.17 | 9.02 | 4.14 |

Example 6

The Application of Dithiodiethanediyldiaminodicarbonyl Dipropionic Acid Dihydrazide (Abbr. DSCDH) for Preparing Hyaluronic Acid Hydrogel:

Hyaluronate Sodium 0.1 g (molecular weight 0.62~1.15 million, NovaMatrix FMC BIOPOLYMER, USA) was dissolved in 10 ml distilled water to give a clear and transparent solution, DSCDH 0.1 g was added into above solution, dissolved under stirring. Then the solution pH was adjusted to 4.75 by adding 0.01 mol/L HCl solution, and 0.05 g 1-ethyl-3-(3-dimethylaminopropyl)carbodiimide hydrochloride (Aldrich, USA) was added and dissolved with stirring. The pH of the reaction mixture was maintained at 4.75 by continuously adding sufficient 0.01 mol/L HCl solution. The viscosity of the solution increased gradually, and a gel formed at ca. 15 minute.

Example 7

The Application of Hyaluronic Acid Hydrogel Cross-Linked by Dithiodiethanediyldiaminodicarbonyl Dipropionic Acid Dihydrazide (Abbr. DSCDH) for Delivery of Vitamin B2:

Hyaluronate Sodium 0.1 g (molecular weight 0.62~1.15 million, NovaMatrix FMC BIOPOLYMER, USA) was dissolved in 10 ml distilled water to give a clear and transparent solution. DSCDH 0.1 g was added into above solution, dissolved under stirring. Then Vitamin B2 0.01 g (Aldrich, USA) was added and stirred evenly (with most of Vitamin B2 dispersed in the solution in the form of solid microparticles). Then the solution pH was adjusted to 4.75 by adding 0.01 mol/L HCl solution, and 0.05 g 1-ethyl-3-(3-dimethylaminopropyl) carbodiimide hydrochloride (Aldrich, USA) was added with magnetic stirring. The pH of the reaction mixture was maintained at 4.75 by continuously adding sufficient 0.01 mol/L HCl solution. The viscosity of the solution increased gradually, and a yellow gel formed in 15 minute.

The above hydrogel (ca. 1 g) was put into a 15 ml glass vial, and 10 ml 0.1 M phosphate buffer solution (pH=7.2) was added. Then the above glass vial was placed in an incubator which simulates the physiological conditions of human body i.e. 37□ of temperature and 100 rpm of rotation speed. At 24 hour intervals, remove the supernatant solution in which the Vitamin B2 content was determined at 440 μm, and add 10 ml fresh 0.1 M phosphate buffer solution (pH=7.2) back.

DSCDH cross-linked hyaluronic acid hydrogel is an effective drug delivery carrier, Vitamin B2 can be gradually released from the hydrogel, and the release time can be as long as 120 hours. Refer to the following table:

| Time (hour) | 24 | 48 | 96 | 120 |
|---|---|---|---|---|
| Percentage of released Vitamin B2 | 43% | 68% | 84% | 93% |

INDUSTRIAL PRACTICALITY

The beneficial effect of this invention is to synthesize many kinds of molecular structure-adjustable compounds with the general formula (I) or (II), which have various flexible molecular structure and many kinds of chemical properties, through such a technical process that the simple diamine having a disulfide linkage and dicarboxylic acid having a disulfide linkage are used as the starting materials and segments with different structure and different chain length are introduced through amide bond. The novel dihydrazide compounds in this invention may well satisfy the application in new chemical modification and chemical cross-linking of materials, and can be used to prepare the new material with reversible crosslinking e.g. new epoxy resin, new medical hydrogel and new drug delivery carrier and new bioactive derivatives of material.

The invention claimed is:

1. Compounds with the general formula (I) or (II):

Wherein, $R_1$, $R_2$, $R_3$ and $R_4$ are selected independently from an alkylene group, a substituted alkylene group, an arylene group or a polyether backbone.

2. The compounds of claim 1, wherein $R_1$ and $R_2$ are $C_1$-$C_{15}$ alkylene group independently.

3. The compounds of claim 1 or 2, wherein $R_3$ and $R_4$ are $C_1$-$C_{15}$ alkylene group independently.

4. The compounds of general formula (I) according to claim 3, wherein $R_1$, $R_2$ are the same $C_2$-$C_4$ alkylene group and $R_3$, $R_4$ are the same $C_1$-$C_8$ alkylene group, and the compounds of general formula (II) according to claim 3, wherein $R_1$, $R_2$ are the same $C_1$-$C_8$ alkylene group and $R_3$, $R_4$ are the same $C_1$-$C_8$ alkylene group.

5. The compounds of claim 1, wherein $R_1$ and $R_2$ are the same phenylene group.

6. The compounds of claim 1 that said polyether backbone is —[(CHR)$_n$O]$_m$— wherein R is a lower alkyl group, n is an integer of 1-4, m is an integer of 1-4.

7. The compounds of claim 6, wherein R is hydrogen, and n represents 2, 3 or 4.

8. A method for preparing compounds of claim 1, wherein said compounds of general formula (I) are prepared from diamine having a disulfide linkage through the following steps: (1) amine-anhydride reaction between diamine having a disulfide linkage and dicarboxylic anhydride to synthesize disulfide-linked dicarboxylic acid having two amide groups, (2) esterification of above disulfide-linked dicarboxylic acid, and (3) hydrazinolysis of above esterification product of disulfide-linked dicarboxylic acid; and said compounds of general formula (II) are prepared from dicarboxylic acid having a disulfide linkage through the following steps: (1) activation of dicarboxylic acid having a disulfide linkage by carbonyldiimidazole, (2) diamidation reaction between the activated compound of dicarboxylic acid having a disulfide linkage and amino carboxylic acid ester, and (3) hydrazinolysis.

9. The preparation method of claim 8, wherein said diamine having a disulfide linkage is selected from the group consisting of cystamine, cystine dimethyl ester, cystine diethyl ester and dithiodianiline; and said dicarboxylic acid having a disulfide linkage is selected from the group consisting of dithiodiacetic acid, dithiodipropionic acid, dithiodibutanoic acid and dithiodibenzoic acid.

10. A method of preparing a medical hydrogel or a drug delivery carrier, comprising the steps of:
dissolving hyaluronate sodium in water to form a first solution;
adding one of said compounds of claim 1 to said first solution to form a second solution;
adjusting the pH of said second solution to 4.75;
adding 1-ethyl-3-(3-dimethylaminopropyl)carbodiimide hydrochloride to the pH-adjusted second solution; and
maintaining the pH of the second solution at 4.75 until a hydrogel forms.

* * * * *

UNITED STATES PATENT AND TRADEMARK OFFICE
CERTIFICATE OF CORRECTION

PATENT NO. : 8,067,636 B2
APPLICATION NO. : 12/516108
DATED : November 29, 2011
INVENTOR(S) : Xiaozheng Shu It is certified that error appears in the above-identified patent and that said Letters Patent is hereby corrected as shown below:

ON THE TITLE PAGE:

At item (73), correct the Assignee as follows:

Change "(73) Assignee: Bioregen Biomedical (Shanghai) Co., Ltd., Shanghai (CN)" to:

-- (73) Assignee: Bioregen Biomedical (Changzhou) Co., Ltd., Changzhou, Jiangsu (CN) --.

Signed and Sealed this
Twenty-sixth Day of June, 2012

David J. Kappos
*Director of the United States Patent and Trademark Office*